(12) United States Patent
Burr et al.

(10) Patent No.: US 12,306,362 B2
(45) Date of Patent: May 20, 2025

(54) PCCT ENERGY CALIBRATION FROM X-RAY TUBE SPECTRA USING A NEURAL NETWORK

(71) Applicant: CANON MEDICAL SYSTEMS CORPORATION, Tochigi (JP)

(72) Inventors: Kent C. Burr, Vernon Hills, IL (US); Nikolay Markov, Vernon Hills, IL (US); Yi Qiang, Vernon Hills, IL (US)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 210 days.

(21) Appl. No.: 18/152,856

(22) Filed: Jan. 11, 2023

(65) Prior Publication Data

US 2024/0230934 A1 Jul. 11, 2024

(51) Int. Cl.
 *G01T 7/00* (2006.01)
 *G06N 3/08* (2023.01)

(52) U.S. Cl.
 CPC .............. *G01T 7/005* (2013.01); *G06N 3/08* (2013.01)

(58) Field of Classification Search
 CPC ................................ G01T 7/005; G06N 3/08
 See application file for complete search history.

(56) References Cited

U.S. PATENT DOCUMENTS

| 6,018,562 A | 1/2000 | Willson | |
| 2010/0193696 A1* | 8/2010 | Blevis | G01T 1/249 250/252.1 |
| 2011/0012014 A1* | 1/2011 | Livne | A61B 6/482 378/207 |
| 2017/0285186 A1 | 10/2017 | Roessl et al. | |
| 2020/0234471 A1 | 7/2020 | Lu et al. | |
| 2020/0379133 A1 | 12/2020 | Burr et al. | |
| 2021/0093286 A1 | 4/2021 | Stierstorfer et al. | |

FOREIGN PATENT DOCUMENTS

| CN | 109697476 A | 4/2019 |
| EP | 3674753 A1 | 7/2020 |
| WO | 2021/253599 A1 | 12/2021 |

OTHER PUBLICATIONS

Extended European Search Report Issued May 6, 2024 in European Application 24151426.4, 10 pages.

* cited by examiner

*Primary Examiner* — Kiho Kim
(74) *Attorney, Agent, or Firm* — Oblon, McClelland, Maier & Neustadt, L.L.P.

(57) ABSTRACT

An apparatus for calibrating a detector, including acquiring an energy spectrum obtained from a scan using an X-ray tube as a source of radiation, estimating calibration parameters, such as a gain and an offset, for each of several channels of the detector by applying the acquired first energy spectrum to inputs of a trained neural network that outputs the calibration parameters, and calibrating each of the plurality of channels using the estimation parameters. The neural network is trained to produce target output calibration parameters, using two or more measurements selected from isotope peak positions, K-edge absorption features, or K-edge emission peaks.

24 Claims, 21 Drawing Sheets

PCCT ENERGY CALIBRATION FROM X-RAY TUBE SPECTRA USING A NEURAL NETWORK

BACKGROUND

Field

The present disclosure is directed to a system and method of calibration in photon counting computed tomography (PCCT).

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

In computed tomography (CT), the spectral characteristic of the detected radiation can be determined using a photon-counting detector, and such a system can be referred to as photon counting computed tomography (PCCT). The radiation detected by the PCCT detector can be used to determine material separation. Photon counting requires a good correspondence between detector measurements and actual photon energy, which is adjusted through detector energy calibrations.

Calibration of PCCT detector energy is typically performed using either monochromatic spectra from radioactive isotopes, such as Americium (Am) and Cobalt (Co) isotopes, K edge absorption of several high Z materials (e.g., lead (Pb), tungsten W)) or K edge fluorescence of several high Z materials. In X-ray absorption spectroscopy, the K-edge is a sudden increase in X-ray absorption occurring when the energy of the X-rays is just above the binding energy of the innermost electron shell of the atoms interacting with the photons. The term is based on X-ray notation, where the innermost electron shell is known as the K-shell. Physically, this sudden increase in attenuation is caused by the photoelectric absorption of the photons. For this interaction to occur, the photons must have more energy than the binding energy of the K-shell electrons (K-edge).

These typical calibration methods require the presence of radioactive materials in the system or require additional mechanics and complications to install and operate metallic foils to perform K-edge absorption or fluorescence calibrations. These methods require readout and electronic modules and corresponding cooling and power capacities, as well as development of required controls and readout software.

The requirement of radioactive materials in the system is especially troublesome. Radioactive sources are expensive and typically need to be frequently replaced, due to relatively short half-life. Also, the use of radioactive sources places additional licensing requirements on CT system users. Thus, it is preferable to minimize use of radioactive materials in calibration.

Accordingly, it is one object of the present disclosure to provide methods and systems for calibration of a PCCT apparatus that does not require the presence of radioactive materials or installation and operation of metallic foils.

SUMMARY

An aspect is a method for calibrating a detector, including acquiring a first energy spectrum obtained from a scan using an X-ray tube as a source of radiation; estimating calibration parameters, for each of a plurality of channels of the detector, by applying the acquired first energy spectrum to inputs of a trained neural network that outputs the calibration parameters; and calibrating each of the plurality of channels using the estimated calibration parameters.

A further aspect is a method for calibrating a detector, including acquiring a first energy spectrum obtained from a scan using an X-ray tube as a source of radiation; training a plurality of different neural networks for corresponding different spatial regions of the detector; estimating calibration parameters, for each of a plurality of channels of the detector, by applying the acquired first energy spectrum to corresponding inputs of the plurality of trained neural networks which output the calibration parameters for the corresponding different spatial regions; and calibrating each of the plurality of channels using the estimated calibration parameters.

A further aspect is an apparatus for calibrating a detector, including processing circuitry configured to acquire a first energy spectrum obtained from a scan using an X-ray tube as a source of radiation; estimate calibration parameters, for each of a plurality of channels of the detector, by applying the acquired first energy spectrum to inputs of a trained neural network device that outputs the calibration parameters; and calibrate each of the plurality of channels using the estimated calibration parameters. The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
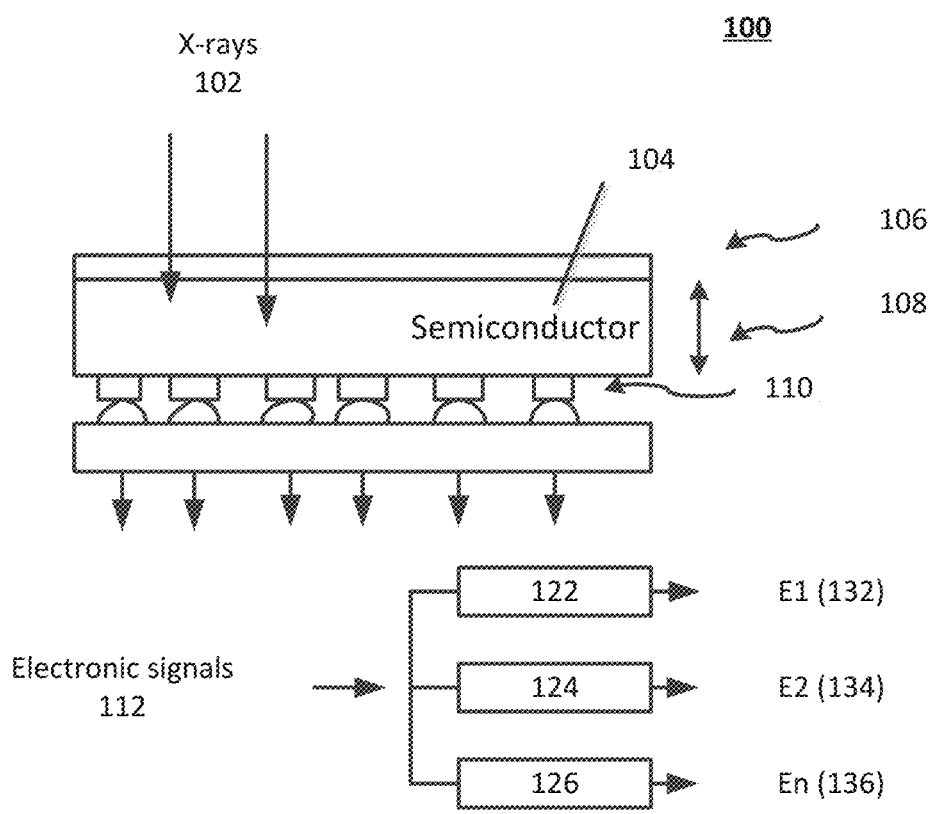
FIG. 1 is a block diagram of a photon counter detector.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

FIG. 1 is a block diagram of a photon-counting detector (PCD) 100, which is a major component of a CT scanner. CT scanners generally use solid state detectors and share similar third-generation rotate-rotate designs. PCDs possess many inherent advantages over other conventional CT detectors because of the fundamental differences in the physical mechanism responsible for photon detection and signal generation.

In particular, PCDs use a direct conversion technology for X-ray detection that does not require a scintillator layer as in energy-integrating detectors (EIDs). The semiconductor detector material 104 of the PCD directly converts X-ray photons 102 into electron hole pairs. A PCD 100 includes a cathode 106, semiconductor material 104 and an anode 110. With a bias voltage 108 applied throughout the semiconductor, electrons travel to and are collected by the anode 110 to generate electronic signals 112.

Semiconductor materials used in PCDs can include cadmium telluride or cadmium zinc telluride, although other materials, such as silicon and gallium arsenide, also have been used. The detector absorption efficiency depends on the detector material used and its thickness. High-atomic-number sensor materials such as cadmium telluride and cadmium zinc telluride have higher absorption efficiency per unit thickness, and subsequently are the most common detector materials used in PCDs.

Because electronic noise usually is detected as a low-amplitude signal, it is interpreted by a PCD as a photon with energy located at the lower end of a typical X-ray spectrum. Thus, by setting a low-energy threshold to be slightly higher than the energy level associated with the electronic noise signal amplitude (e.g., 25 keV), electronic noise can be excluded readily from the measured count data. Since a signal with an energy level lower than this threshold is very unlikely to be caused by a primary photon transmitted through the imaging object of interest, it typically does not contain meaningful information vital to any clinical task. However, electronic noise can have some effect on the detected energy spectrum, because its signal amplitude is added to that of a detected photon, which consequently artificially increases the energy of the detected photon.

Since PCDs use direct conversion technology, detector pixels can be designed without a mechanical separation (septum), which inherently improves the geometric dose efficiency. One specific aspect of PCCT is its ability to allow simultaneous acquisition of high-spatial-resolution and multi-energy images.

PCDs count the number of individual photons that exceed a specified energy level. For a given X-ray photon, the pulse height of the signal created by the charge collection at the anode 110 is proportional to the energy of the photon. Thus, the signal 112 from a PCD carries with it energy information about each individually detected photon. The output signal from a PCD is processed by multiple electronic comparators and counters 122, 124, and 126, where the number of comparators and counters depends on the electronic design of the PCD and its application specific integrated circuits (ASICs). Each detected signal is compared with a voltage that has been calibrated to reflect a specified photon energy level (132, 134, and 136), referred to as an energy threshold. When the energy level of a detected photon exceeds an energy threshold associated with a counter, the photon count is increased by one. In this manner, the number of photons that have energy equal to or greater than a specified energy level is measured. This process is enabled by the very fast ASIC, a key element in PCDs.

By introducing additional energy thresholds above the low-energy threshold, the output of a PCD can be divided into several discrete energy bins. Each registered photon is thus assigned to a specific bin depending on its energy, such that each pixel measures a histogram of the incident X-ray spectrum. The difference between such "open" bins (from a threshold to infinity) is calculated, and, as a result, the detector reports the number of photons in the "closed" bins (from a lower threshold to a higher threshold). Using more than two energy bins allows discrimination between, on the one hand, dense bone and calcifications and, on the other hand, heavier elements (commonly iodine or gadolinium) used as contrast agents. Note also that the detector outputs its measurements in terms of energy bins internal to the detector. The calibration process is required to build a correspondence between these bins and the actual absolute energy that is measured.

Figure 5:
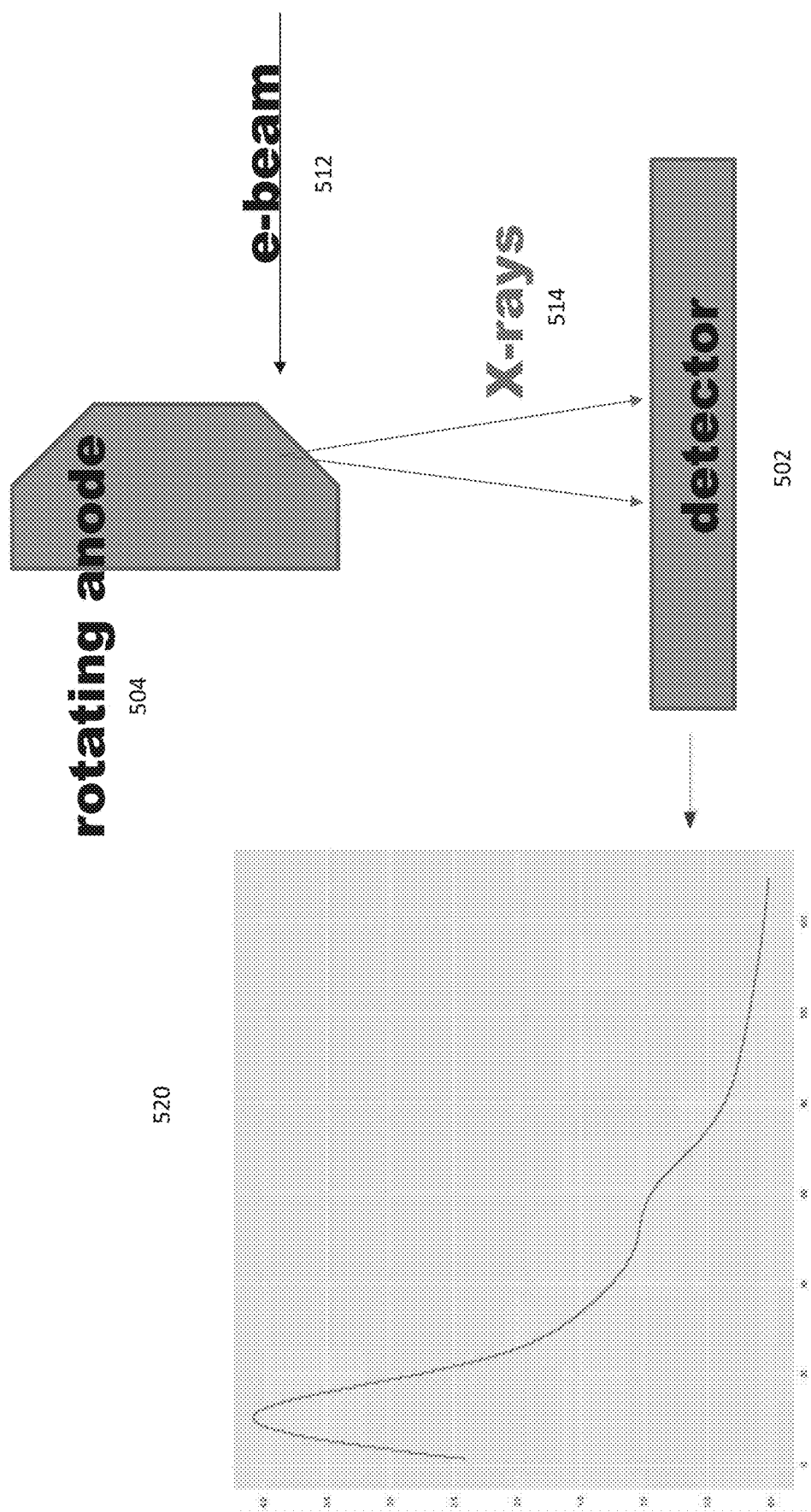
FIG. 5 illustrates a system for producing an X-ray energy spectrum for a certain energy of an X-ray tube.

A calibration system and method of a PCCT of the present disclosure does not require the presence of radioactive materials or installation and operation of metallic foils. Disclosed embodiments are a calibration system and method that uses a neural network having an input of the full-tube X-ray spectrum with a predetermined tube voltage to perform energy calibration. The calibration system and method replace calibration using isotope sources (such as Am241 and Co57) with the generation of calibration parameters based on X-ray tube spectra that are processed by a neural network. The calibration system and method execute an energy scan at a known X-ray tube voltage. In one embodiment, an energy scan is sought in which the thresholds of the counters are stepped through a range of values to obtain a spectrum with a large number of narrowly-spaced energy bins which provides resolution that is superior to the typical small number of wide energy bins available in low-power production electronics. We refer to this type of energy scan, with narrowly-spaced energy bins, as a full resolution energy scan. The energy spectrum 520 in FIG. 5 is an example of the output of a full resolution scan. In the one embodiment, the method executes several (at least two) energy scans with different X-ray tube voltages to obtain several calibration points. In order to perform the method, the neural network is trained to analyze spectra and set correspondence between an energy bin in the detector and actual gamma energy. In one embodiment, since the relation is shown to be linear, this correspondence can take the form of gain and offset parameters. Subsequently, the trained neural network outputs one of the gain and the offset for every pixel, or isotope peak positions that are used to calculate the gain and offset. The method can be extended to accept data from a limited number of energy bins (e.g., six) to use standard PCCT energy binning schema and data-taking procedures.

Figure 2:
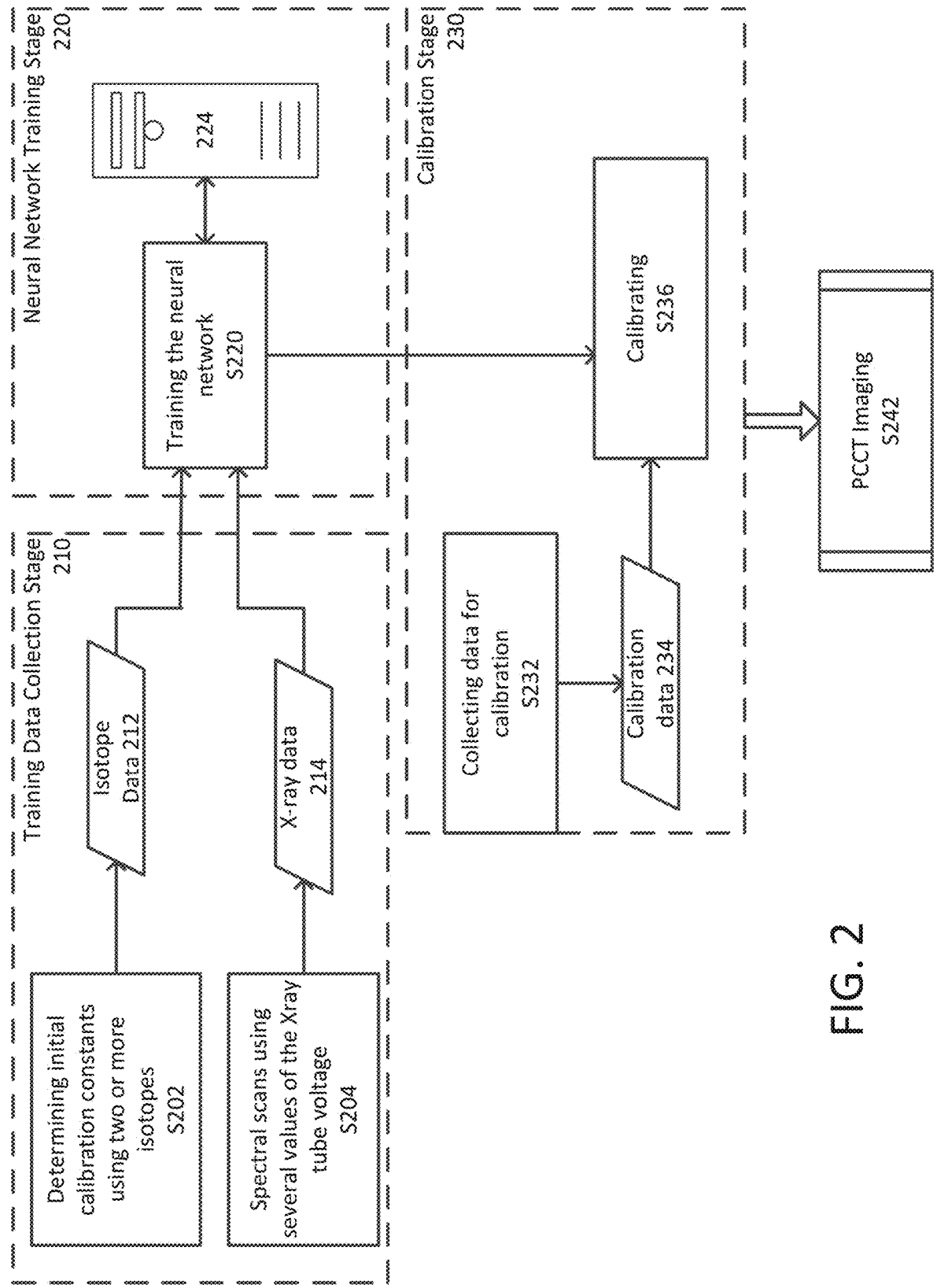
FIG. 2 is a flowchart of a method for performing initial PCCT energy calibration in accordance with an exemplary aspect of the disclosure.

FIG. 2 is a flowchart of a method for performing initial PCCT energy calibration in accordance with an exemplary aspect of the disclosure. PCCT energy calibration is performed using a neural network. Training data for the neural network is collected during a training data collection stage 210. In a preferred embodiment, training data sets must consist of many matched sets of (a) isotope data and (b) X-ray tube data, constituting spectra sets, acquired for a same pixel, using the same CT. The CT electronics setup for obtaining the isotope data is preferably able to take full resolution energy scans, so that the target training outputs (e.g., isotope peak positions or, equivalently, gain and offset) can be determined with high accuracy. The CT electronics can be installed either in a manufacturer's factory or an R&D lab. It is not necessary that the electronics setup be a part of a PCCT scanner.

In one embodiment, the training data includes calibration constants (Isotope data 212) that are determined, in step S202, based on two or more different isotopes. In an alternative embodiment, the training data can include two or more energy features corresponding to K edge absorption or K edge fluorescence.

In step S204, spectral scans are performed using several values of the X-ray tube voltage to obtain X-ray data 214. In particular, spectral scans are performed using a CT scanner setup with a minimum of two values of the X-ray tube voltage. The spectral scans are done in nominal energy bins, as coarse binning, in about 6 bins over the full energy range, for example. The spectral scans are either directly acquired in coarse bins, or post-processed into coarse bins.

In step S220, the neural network 224 is trained using the training data. The isotope data 212 from the initial data collection and the X-ray data 214 from the initial spectral scan using PCCT are used to train the neural network 224 to recover the target output calibration constants using the X-ray data 214 as input to the neural network.

Once the neural network 224 has been trained to a preferred error rate and accuracy, the trained neural network is used in a calibration stage 230. In the calibration stage 230, the PCCT scanner to be applied to actual patients is used. It is not necessary that the PCCT scanner take full resolution energy scans. The functionality of full-resolution scanning is not required for the calibration procedure. Instead, for purposes of the calibration scan, the scanner configuration preferably closely replicates the CT scanner setup that was used during the training data collection stage 210.

In step S232, data is collected for calibration. Spectral scans are performed using a PCCT scanner with a minimum of two values of the X-ray tube voltage. The spectral scans are performed in nominal energy bins, coarse binning at about 6 bins over the full energy range and used to determine calibration data 234. A CT scanner is used for spectral scans in the end-use medical environment. The configuration of the PCCT scanner for calibration must replicate the CT scanner setup for the medical environment, as closely as possible, including, but not limited to, the absence of the wedge between the X-ray tube and detector and using a same type of the X-ray tube in both setups.

In step S236, in the case of using two isotopes for the training data, the trained neural network can either determine a gain and an offset parameter for each pixel using the calibration data 234 obtained from the PCCT scanner or the peak position, from which the gain and offset are calculated.

In step S242, gain and offset parameters are used for every pixel and incorporated into the operation of the PCCT imaging. In particular, PCCT imaging is performed based on the calibration in step S242.

Figure 3:
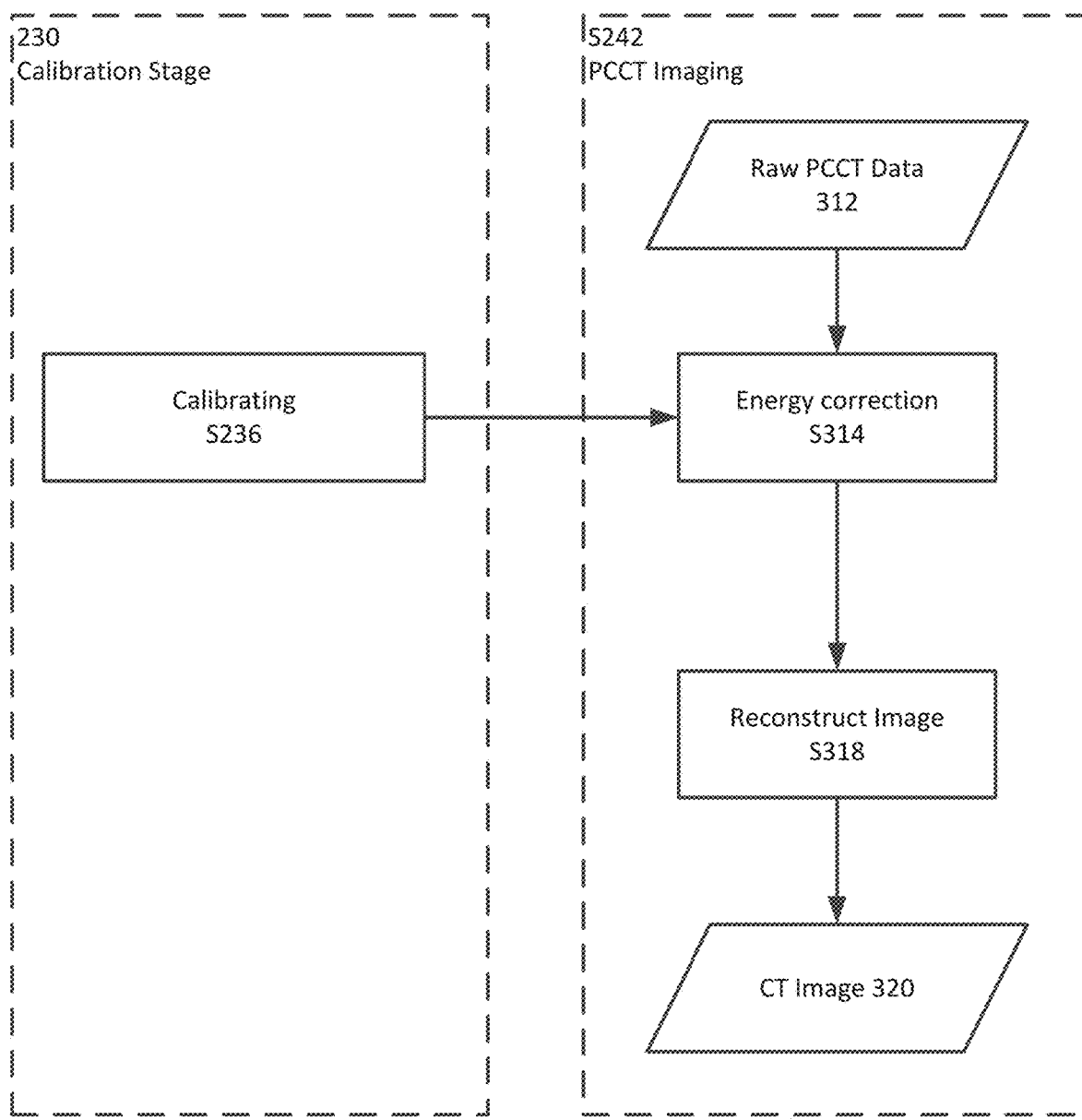
FIG. 3 is a flowchart of the PCCT imaging step.

FIG. 3 is a flowchart of the PCCT imaging step S242, which include an energy calibration process S314 for applying energy correction to raw PCCT data 312 using previously determined calibration parameters, and a step S318 for reconstructing a CT image 320 from the corrected PCCT data. In one embodiment, step S236 is performed less frequently than step S314. For example, in one non-limiting implementation, step S236 can be performed once for each different CT scanner and the resultant energy calibration parameters can be used in several different scans by that CT scanner.

In PCCT imaging step S242, the raw PCCT data 312 is corrected in process S314 using the results of energy calibration step S236. Then, in step S318, a CT image 320 is reconstructed from the corrected energy data using an image reconstruction process.

In some embodiments, the training data can be expanded to include three or more radioactive isotope peaks in the training data. In one embodiment, a calibration function with more than two parameters is used, enabling application to a non-linear calibration function.

Figure 4:
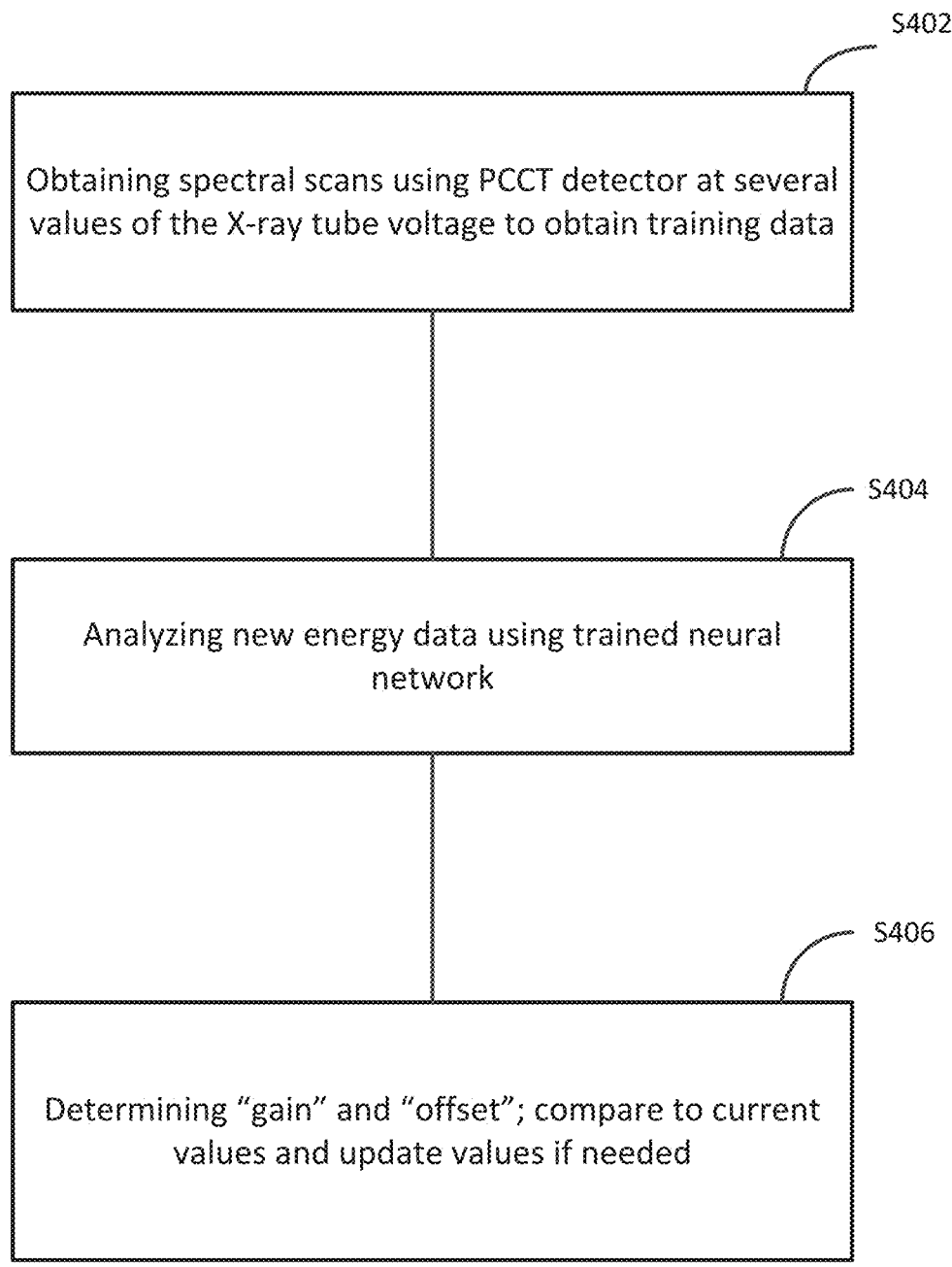
FIG. 4 is a flowchart of a method for performing recalibrations in accordance with an exemplary aspect of the disclosure.

FIG. 4 is a flowchart of a method for performing recalibrations in accordance with an exemplary aspect of the disclosure. The disclosed calibration method is not limited to an initial calibration of the PCCT detector, but can be performed periodically in order to update the detector parameters.

The recalibration method includes, in step S402, performing spectral scans and obtaining detection data with the PCCT detector for several different values of the X-ray tube voltage.

In step S404, the detection data is used by the neural network to analyze the data.

The neural network, in step S406, determines gain and offset parameters for each pixel. The newly obtained gain and offset parameter values are compared to previous gain and offset parameter values, and are used to update the gain and offset parameter values, in particular when the differences are above a predetermined difference.

FIG. 5 illustrates a system for producing an X-ray energy spectrum for a certain voltage of an X-ray tube. The photon-counting computed tomography (PCCT) detector 502 receives X-ray from an X-ray tube of the CT scanner. The CT scanner uses a motorized X-ray source 504 that rotates around the circular opening of a donut-shaped structure called a gantry. During a CT scan, the X-ray tube rotates and emits narrow beams of X-rays 514. The CT scanner uses the X-ray detector 502, which is located directly opposite the X-ray source. The X-rays 514 are detected by the detector 502 and corresponding signals are transmitted to processing circuitry. The processing circuitry generates an X-ray energy spectrum 520 for a certain voltage of the X-ray tube.

Figure 6:
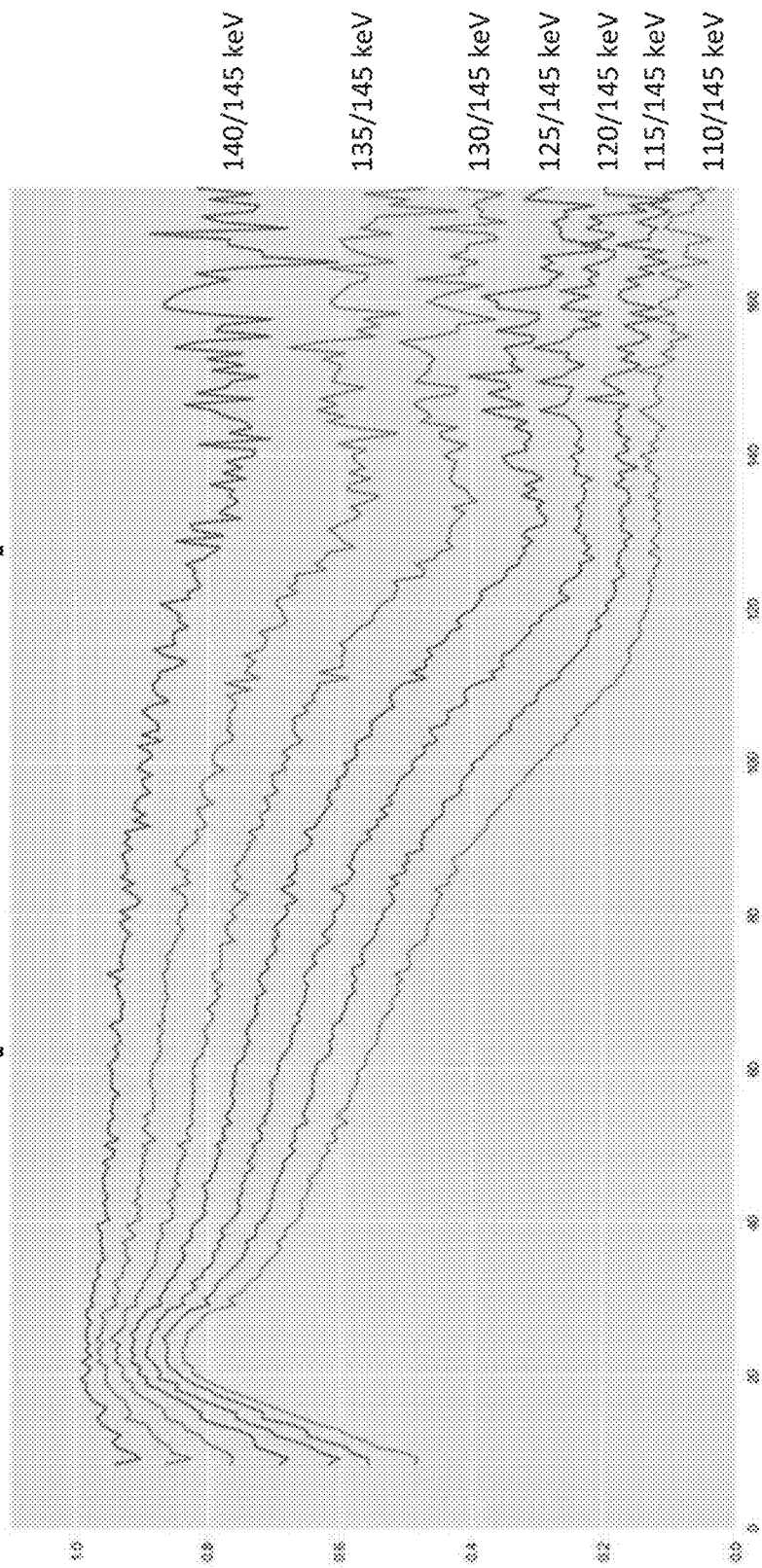
FIG. 6 is a graph of ratio of spectra for different X-ray tube voltages.

FIG. 6 is a graph of various ratios of spectra for different X-ray tube voltages. X-ray radiation with different X-ray tube voltage levels will have different spectra while exhibiting no sharp features, which would make the spectral features easy to identify and use for calibrations using traditional analytic methods. Typically, a range of X-ray tube spectra would cover an entire operating range (i.e., low energy up to or slightly past maximum normal-operating kVp for the X-ray tube). In one embodiment, a difference in shape between different spectra is identified using machine learning tools and the difference in shape is used for the calibration. Ultimately, the difference in shape is used to establish a correspondence between the channel in the detector output and X-ray energy in keV. Additional energy spectra with characteristic structures added through filtering of X-ray tube emission can be included as well (e.g., transmission spectrum with K-edge materials or other filters).

Figure 7:
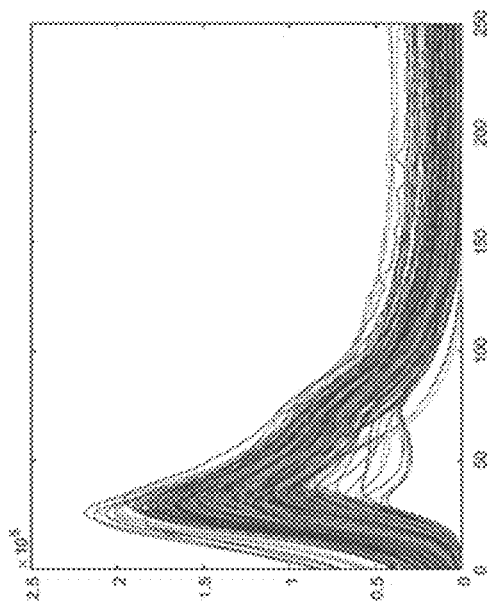
FIG. 7 illustrates data pre-processing to smooth the measured spectra.
Figure 7:
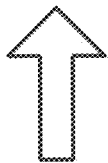
Figure 7:
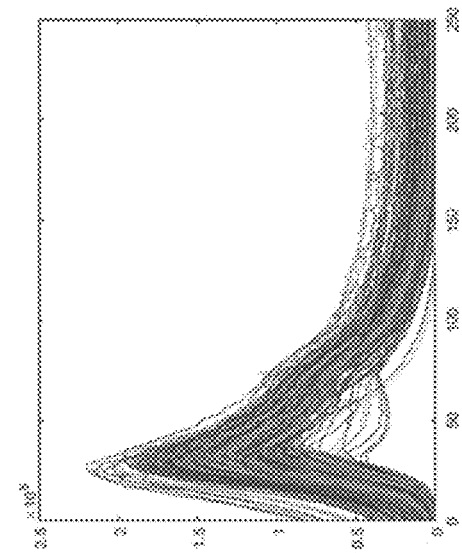

In some embodiments, data pre-processing is performed in order to improve the performance of the neural network. FIG. 7 illustrates data pre-processing to smooth the measured spectra. Measured spectra can be smoothed by performing convolution with a Gaussian having a width that is sufficient to remove artificial features and noise that could degrade neural network performance.

Figure 8:
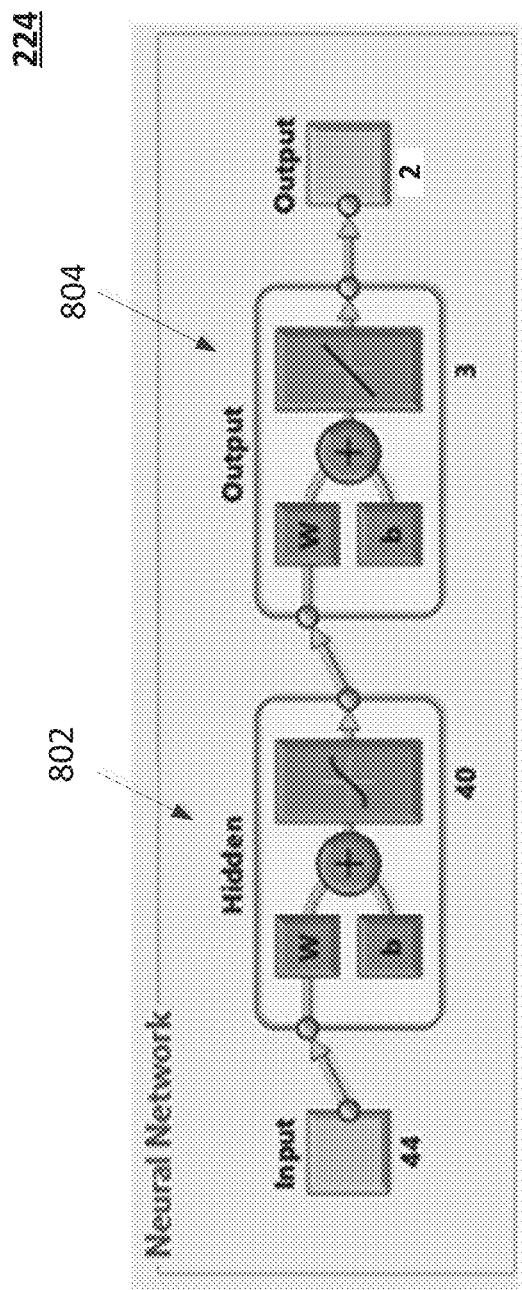
FIG. 8 is an architecture for a neural network for PCCT energy calibration in accordance with an exemplary aspect of the disclosure.

FIG. 8 is an architecture for a neural network for PCCT energy calibration in accordance with an exemplary embodiment of the present disclosure. In one embodiment, the neural network 224 contains a single hidden layer 802 and a linear output layer 804. In one non-limiting example, the inputs to the network are a number of samples from the 110 kVp spectra, the 145 kVp spectra, or the ratio of the two spectra. However, it should be understood that additional spectra, at other keV and/or different acquisition times, can be included in the training data. During training of the neural network, the target output is the measured peak positions of two isotopes, preferably Am241 and Co57 peaks.

The neural network for PCCT energy calibration determines calibration parameters that are sufficient for calibration of a PCCT detector without the need for using radioactive materials during the calibration. However, the neural network is not limited to determining a linear function. A multilayered neural network can be trained with three or more radioactive isotope peaks or positions of the K edge peaks of the different materials in the training data to determine parameters of a non-linear model. The calibration function can include more than two parameters for a non-linear function.

In one embodiment, after training, the output of the neural network is used to determine a gain and an offset for each pixel. The gain and the offset are used for energy calibration of the PCCT detector. The performance of the neural network is evaluated by applying the gain and the offset to the fit Am241 and Co57 peak positions for each corresponding pixel, and generating histograms of the estimated Am241 and Co57 peak positions (in keV).

Figure 9:
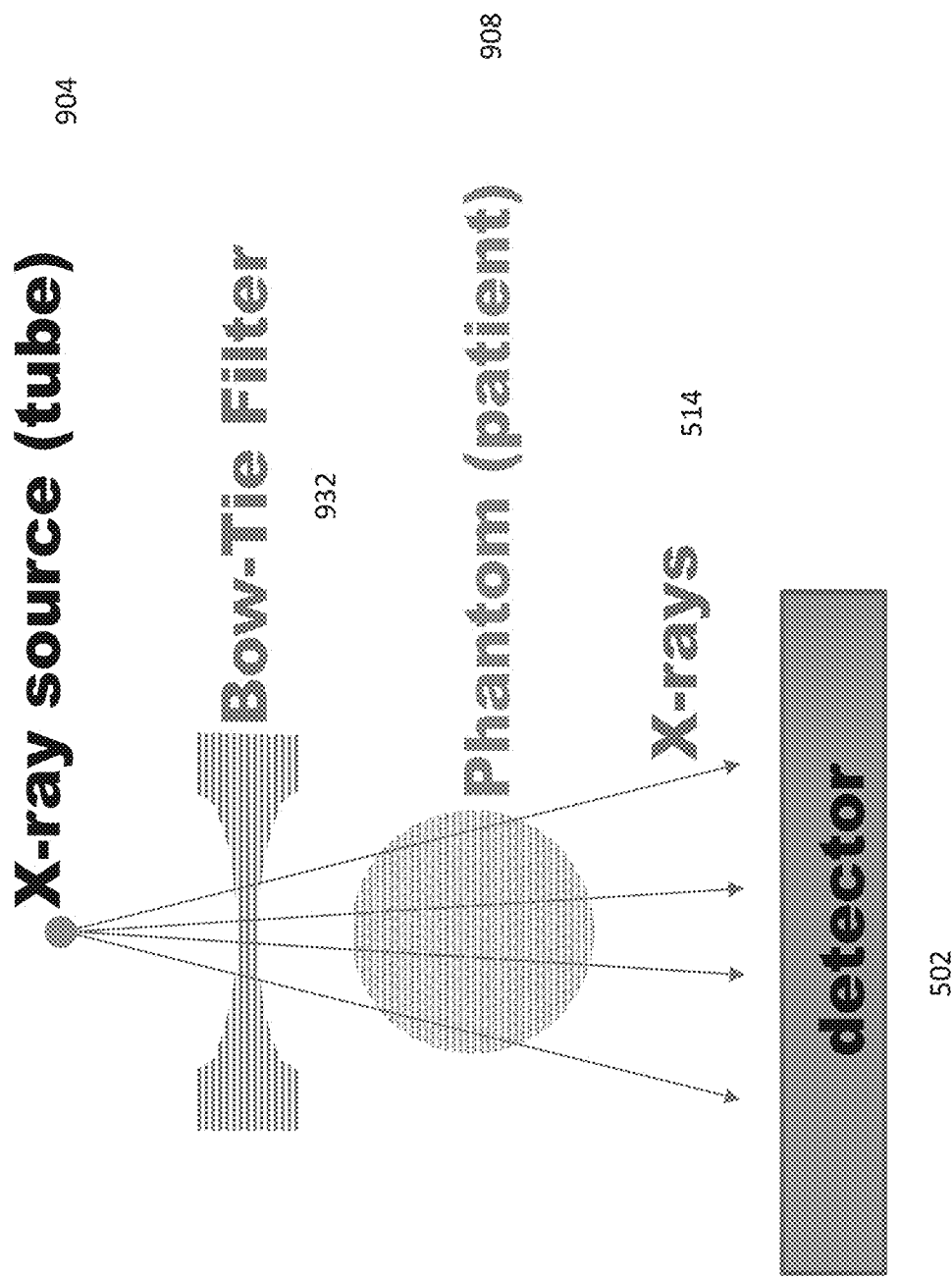
FIG. 9 illustrates a CT scanning system equipped with a bow-tie filter.

Other components of the CT scanning system can also affect performance of the neural network. The effects of the other components can be used to refine the neural network. For example, FIG. 9 illustrates a CT scanning system equipped with a bow-tie filter. A bow-tie filter 932 is a component of a CT scanning system that can be placed between the X-ray source 904 (tube) and a phantom 908 (or patient) to make the X-ray intensity equal across the surface of the photon-counting detector 502. However, in addition to modifying the X-ray intensity, the bow-tie filter 932 also modifies the X-ray spectrum. In particular, the bow-tie filter has a beam-hardening effect because the absorption of the bow-tie material varies with energy.

FIG. 5 can be used to explain the "heel effect." X-rays emitted by the X-ray source at different angles pass through different amounts of anode material and, therefore, are subject to different amounts of filtering, which has a large effect on the X-ray intensity vs. angle and is referred to as the "heel effect". These differing amounts of filtering also affect the spectral content of the X-rays, which is the beam-hardening effect.

The use of bow-tie filters and spectral filtering due to the spectral heel effect can result in inconsistencies and variation in the X-ray spectrum across the surface of the detector. Various approaches can be used to alleviate these effects. One approach is to add additional inputs to the neural network model that represent the (x, y) pixel position within the field of the X-ray emission. For example, a row and column number of a pixel in the overall CT detector array can be added as inputs to the neural network. Another approach is to include additional inputs to the neural network model representing the thickness and the material of the bow-tie filter, e.g., an input of mm for thickness, and a charge number for material. A further approach is to train different neural networks for different spatial regions of pixels of the field-of-view. In this approach, geometric symmetry in the CT system causes symmetry between different neural networks and can be used to reduce the total number of required networks.

During early periods of development of a neural network model, before large amounts of data are available from multiple full CT detectors, training data can initially be generated by moving a small number of detector modules to known locations within the X-ray tube emission field. This can be done, for example, with an x-y-translation stage or by building a fixture that allows a module to be placed at a number of fixed positions within the X-ray tube emission field. In this way, a small number of modules can be used to acquire data that covers the range of variation expected from the bow-tie and the heel effect. During acquisition of the training data, the position of the module can be recorded and later translated to an absolute position within the overall future CT detector array for each pixel in the module. When this method is used to generate training data, it is preferable to have the total geometric training range extend beyond the expected geometric range of the final CT detector. This extended training range can improve the robustness of the neural network response.

If the CT scanning system includes multiple bow-ties, or spectral filters, other approaches can be taken. One approach is to train a different neural network for each bow-tie/filter combination. A further approach is to add neural network inputs that represent the bow-tie and the spectral filter choice. For example, inputs with values of (e.g., 1 or 2) can be added for a two-choice bow-tie selection, and input with values (e.g., 1, 2, or 3) can be added for a three-choice filter selection. A further approach is to add additional inputs to the neural network that represent the thickness and material of the bow-tie filter (e.g., mm for thickness, and charge number for material). Then the neural network can naturally be generalized to different bow-tie filters.

Figure 10:
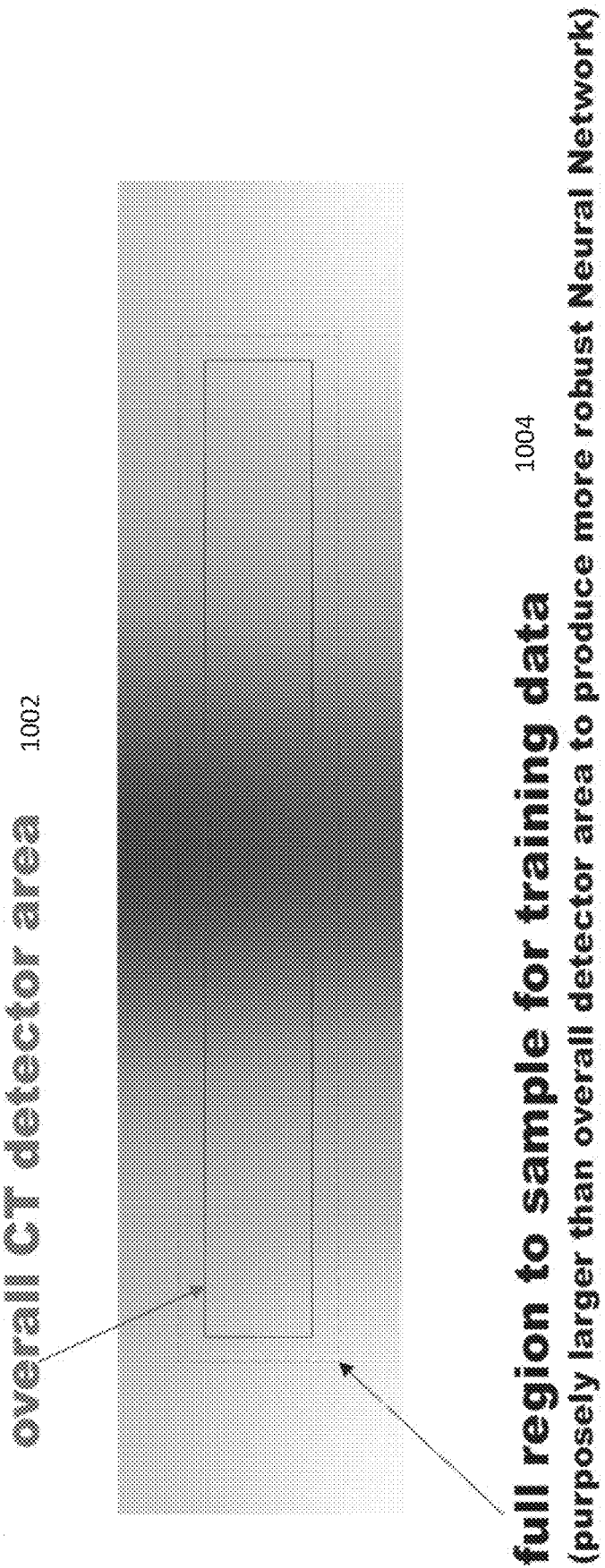
FIG. 10 illustrates an example of spectral content of X-ray for training the neural network in accordance with an exemplary aspect of the disclosure.

FIG. 10 illustrates a spatial variation of the spectral content of X-rays on a detector. In one embodiment, the full region 1004 for training data is purposely made larger than the overall detector area 1002 to produce a more robust neural network model.

Figure 11:
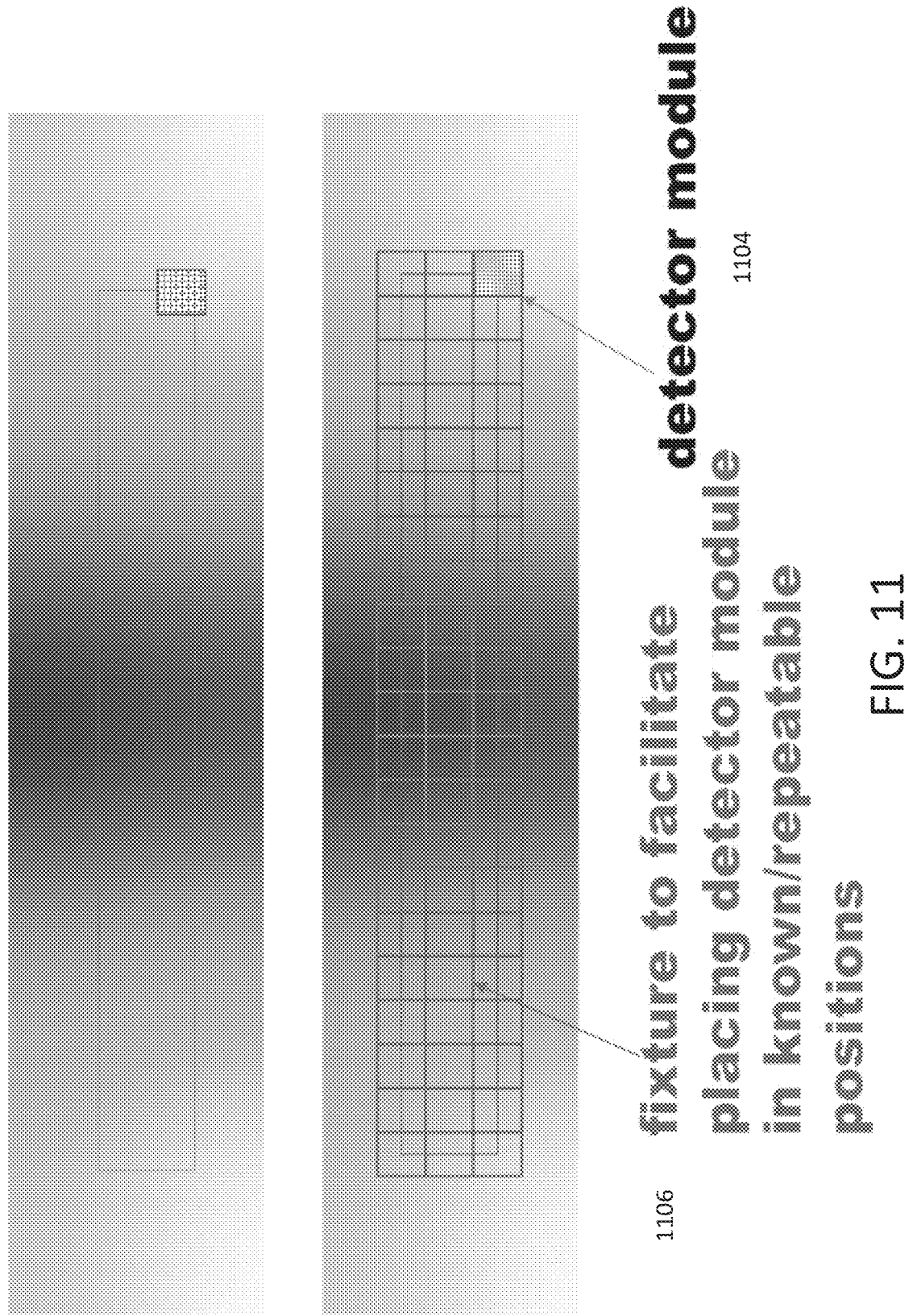
FIG. 11 illustrates placement positions of a detector module in accordance with an exemplary aspect of the disclosure.

FIG. 11 illustrates a spatial variation of the spectral content of X-rays on a detector. In one embodiment, a fixture allows a module to be placed at a number of fixed repeatable positions within the X-ray tube emission field. In particular, the detector module 1104 can be guided to known positions 1106 by a fixture that facilitates the placement.

Figure 12:
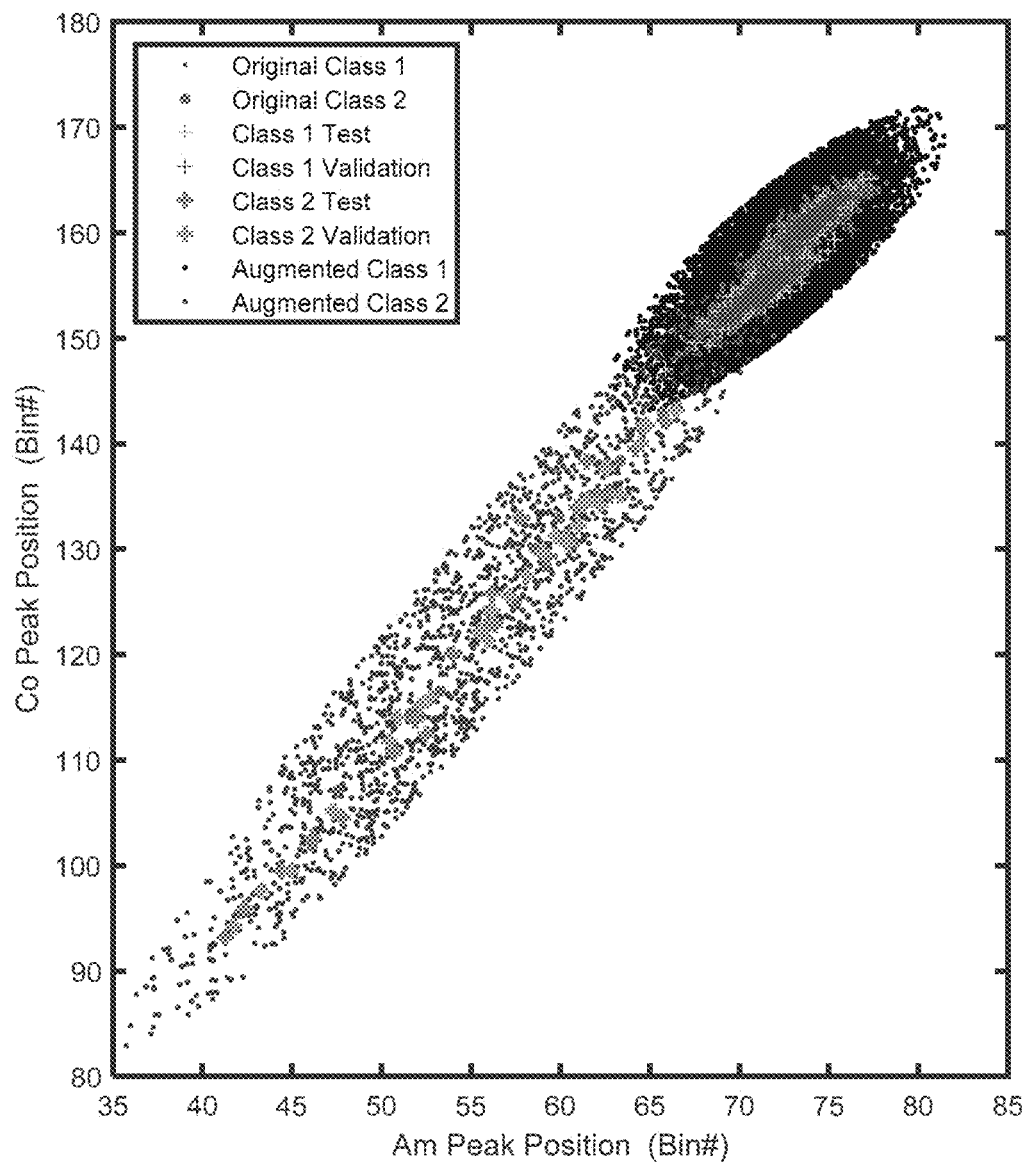
FIG. 12 is a graph of augmented training data in accordance with an exemplary aspect of the disclosure.

FIG. 12 illustrates data augmentation to increase the amount of training data used to train the neural network model. To increase the probability that a neural network will generalize well with new input data that is somewhat outside the range of data currently available, existing training data can be augmented. Training data can be augmented using the measured Am241 and Co57 peak positions. Using the measured peak positions, each available X-ray spectrum is calibrated for each pixel. Training data can be augmented by generating, multiple times for each pixel, new random Am241 and Co57 peaks positions, which cover a wider range than seen in the original distributions. In this augmentation approach, the calibration equation is inverted and the linear transformation is applied to the resulting calibrated spectra to generate new spectra. In a further augmentation approach, the transformed spectra can be used as new input. In this case, corresponding randomly chosen peak positions can be used as new target output. In a further approach, test data as well as validation data are taken only from the original training data.

Figure 13:
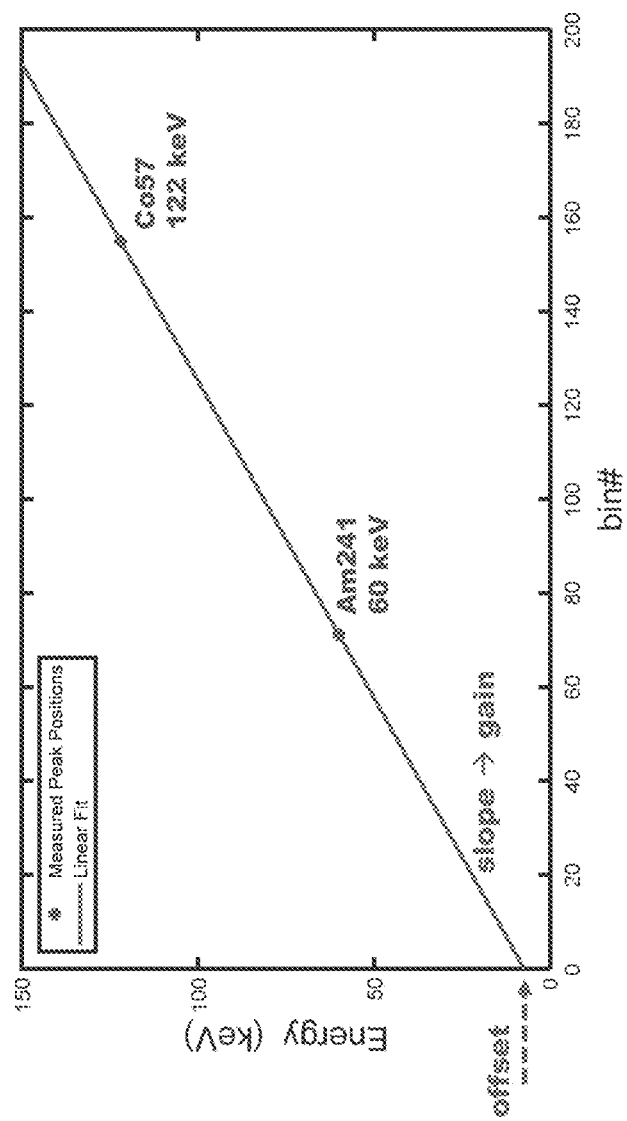
FIG. 13 is a graph of an example linear relation for energy vs. bin number in accordance with an exemplary aspect of the disclosure.

In one embodiment, the energy calibration is based on a linear equation that fits the measured Am241 peak position and the measured Co57 peak position. FIG. 13 is a graph of a non-limiting example linear relation for energy vs. bin number. The linear relation shown in FIG. 13 is for a 60 keV Am241 peak position and a 122 keV Co57 peak position. It should be understood that other isotope peaks can be applied, but the basic linear relation still holds. The linear relation is used to determine a gain and offset for a single pixel. The linear relation is:

$$\text{Energy } (keV) = \text{gain} * \text{bin\#} + \text{offset}$$

where the offset is the energy intercept and the gain is the slope of the line through the Am241 and Co57 peak positions. In the equation above, the linear relationship is explicitly parameterized by a gain and offset, which may be referred to as slope-intercept form, with the gain being the slope and offset being the intercept. Alternatively, the same linear expression can be parameterized in point-slope form, where one point (e.g. Am241 or Co57 peak position, or position of another chosen energy) and the slope (e.g., the gain) are specified, or can be parameterized in two-point form, where two points (e.g. Am241 and Co57 peak positions, or position of two other chosen energies) are specified. For the purposes of this disclosure, any combinations of such parameters can be referred to as calibration parameters. In one embodiment, the energy calibration is based on a nonlinear equation.

Figure 14B:
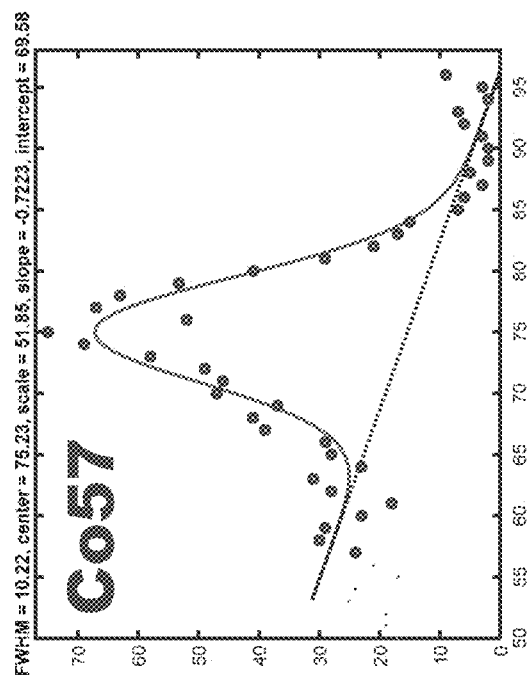
FIGS. 14A and 14B are graphs to explain determining peak positions from isotope spectra obtained in an exemplary method for obtaining target output for neural network training.
Figure 14A:
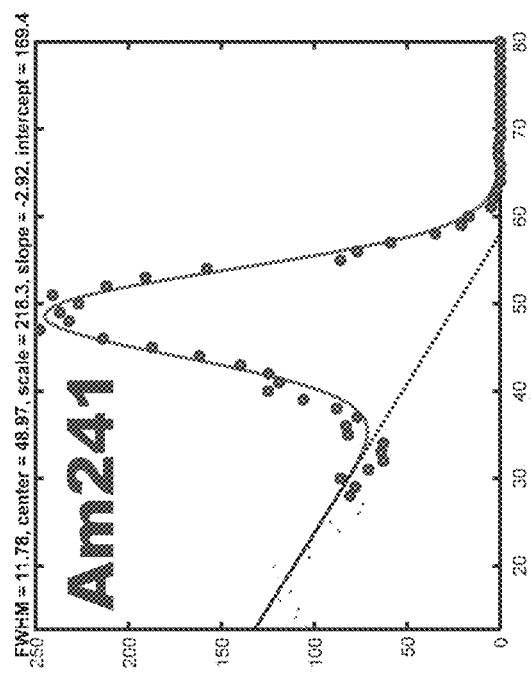

FIGS. 14A and 14B are graphs to explain pre-processing performed in the determination of peak positions. The pre-processing can include performing interpolation to generate a curve from sample points, for each isotope, e.g., Am241 and Co57. After performing interpolation, peak positions of each isotope can be determined by fitting a region near the peak to the sum of a Gaussian and a linear background.

Figure 15:
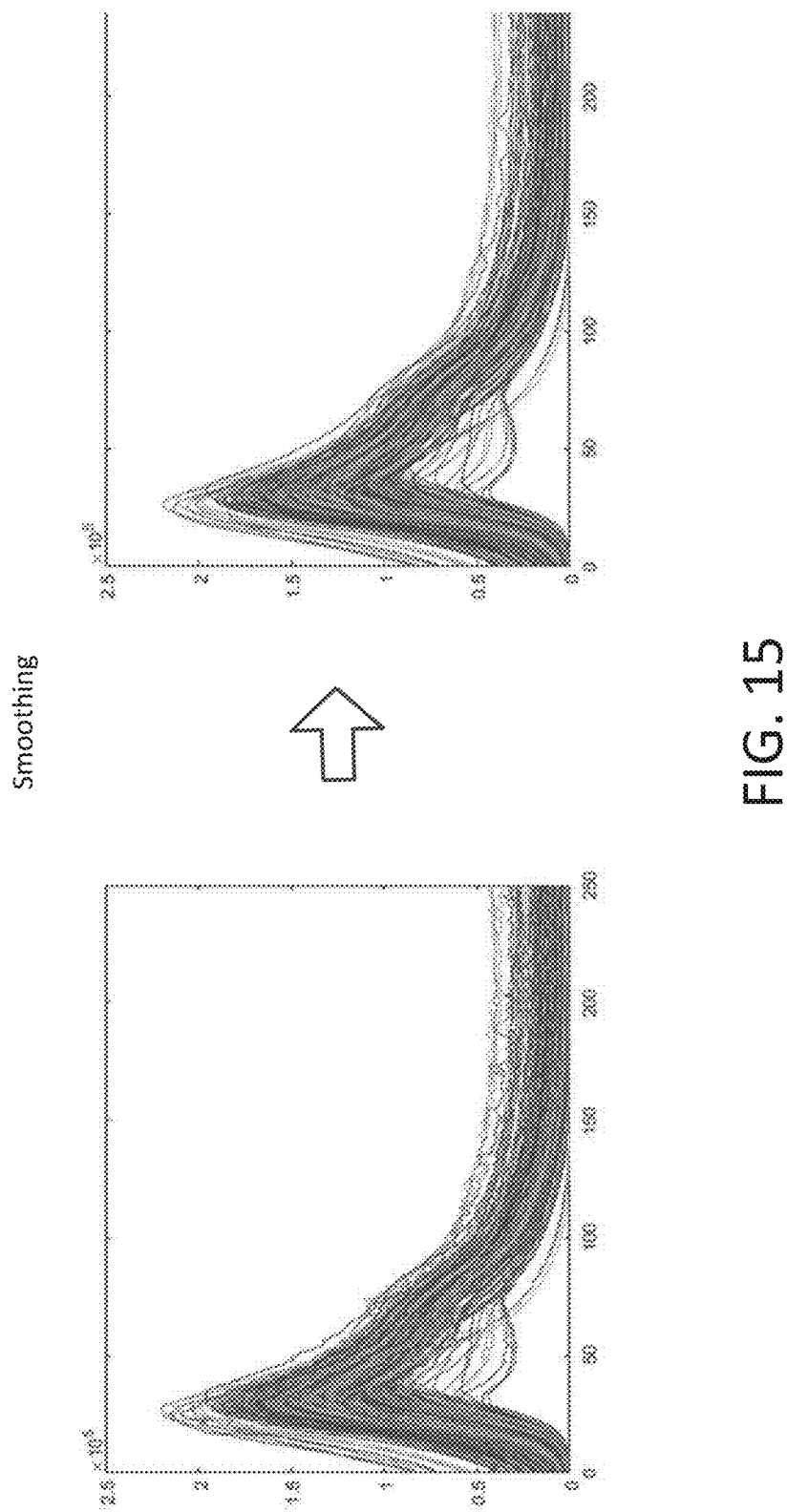
FIG. 15 includes graphs illustrating a pre-processing step of smoothing the spectra by convolution.

FIG. 15 illustrates a pre-processing step of smoothing the X-ray spectra. The X-ray spectra can be further processed to smooth by performing a convolution with a Gaussian, for example, a Gaussian having a full width at half maximum (FWHM) of 4 bins.

Figure 16A:
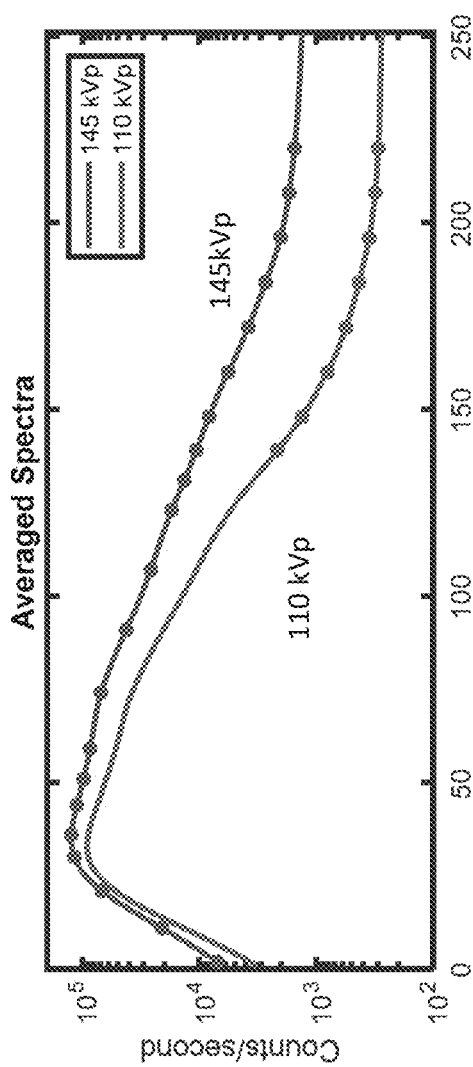
FIGS. 16A and 16B are graphs illustrating neural network inputs.
Figure 16B:
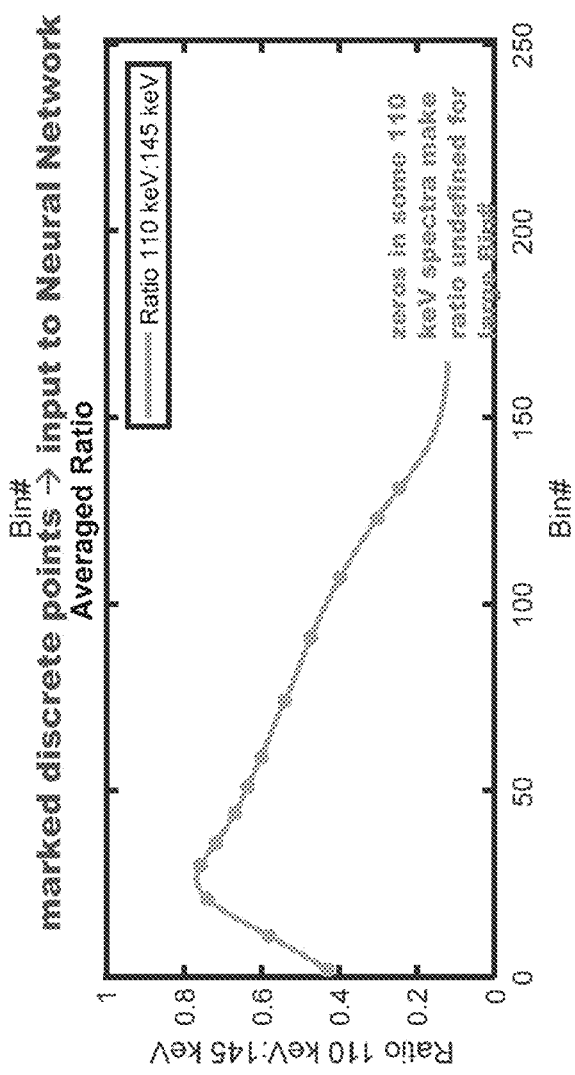

The pre-processed data are used as training data for the neural network. The input data for the neural network can be used as training, validation, and test data. The input data can be arbitrarily-chosen samples from an X-ray spectra for an isotope. As shown in FIG. 16A, input data can be samples from the 110 kVp spectra or the 145 kVp spectra, for example. In one embodiment, as shown in FIG. 16B, the input data is the ratio of two spectra, e.g., 110 kVp to 145 kVp. In one embodiment, the target output for training a neural network is the measured peak positions of the isotope peaks (in bin #), for example, measured peak positions of the Am241 and Co57 peaks, estimated by the pre-processing steps. The output from the trained neural network is used to determine the gain and the offset for each pixel of the detector.

In one embodiment, a neural network model is created using a library function for neural network training, for example the MATLAB Fitnet function or the like. The data of each isotope spectra is divided into training, validation, and test sets. The Bayesian Regularization training algorithm is used. Training is terminated when the validation results fail to improve for a fixed number of epochs. The performance of the Neural Network is evaluated by applying the 'gain' and 'offset' to the fit Am241 and Co57 peak positions for each corresponding pixel and generating histograms of the estimated Am241 and Co57 peak positions (in keV).

Figures 17A, 17B:
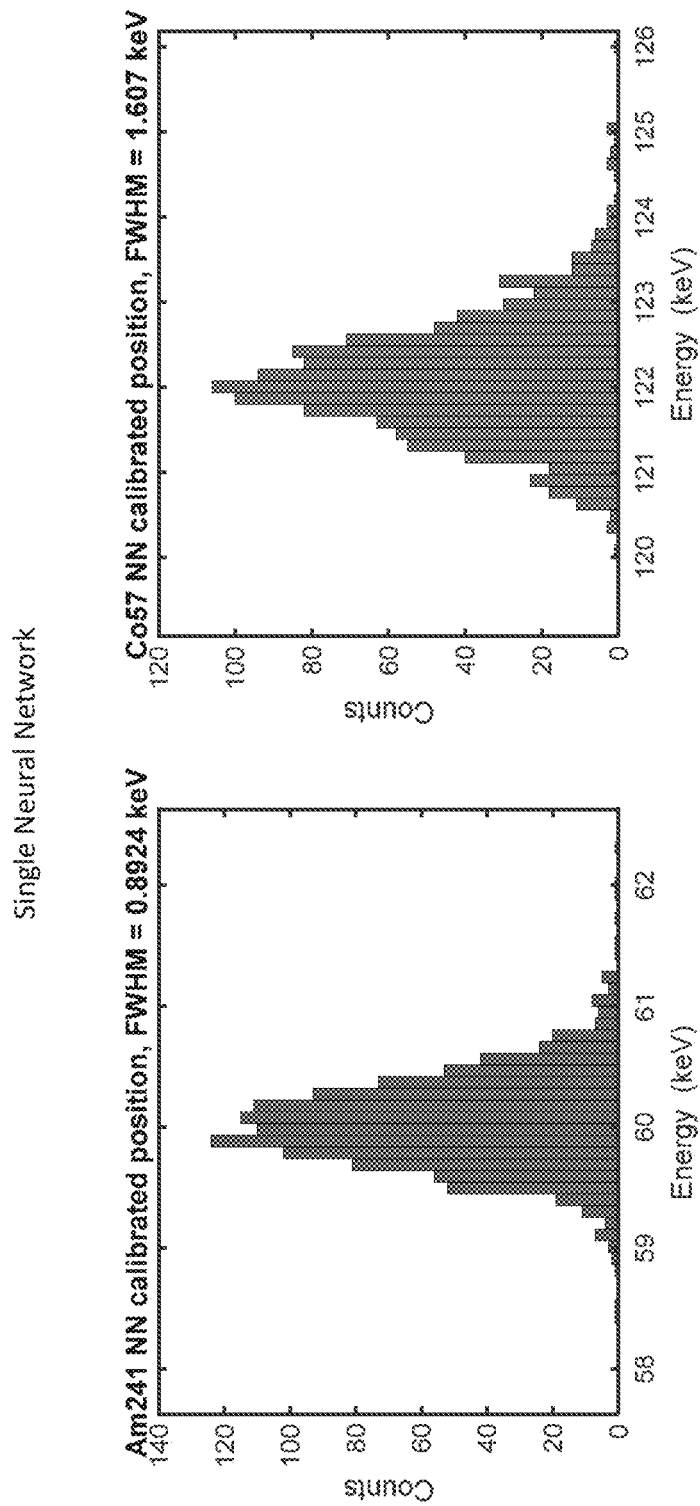
FIGS. 17A and 17B are charts showing histograms of estimated peak positions for each isotope when x-ray tube data is input to a trained neural network.

FIGS. 17A and 17B are histogram charts of the calibrated peak positions for Am241 and Co57, respectively. In one embodiment, individual neural networks are trained for each isotope. FIG. 17A is a histogram of validation and test pixels (as calibrated) for the Am241 neural network. FIG. 17B is a histogram of validation and test pixels (as calibrated) for the Co57 neural network.

Figure 18B:
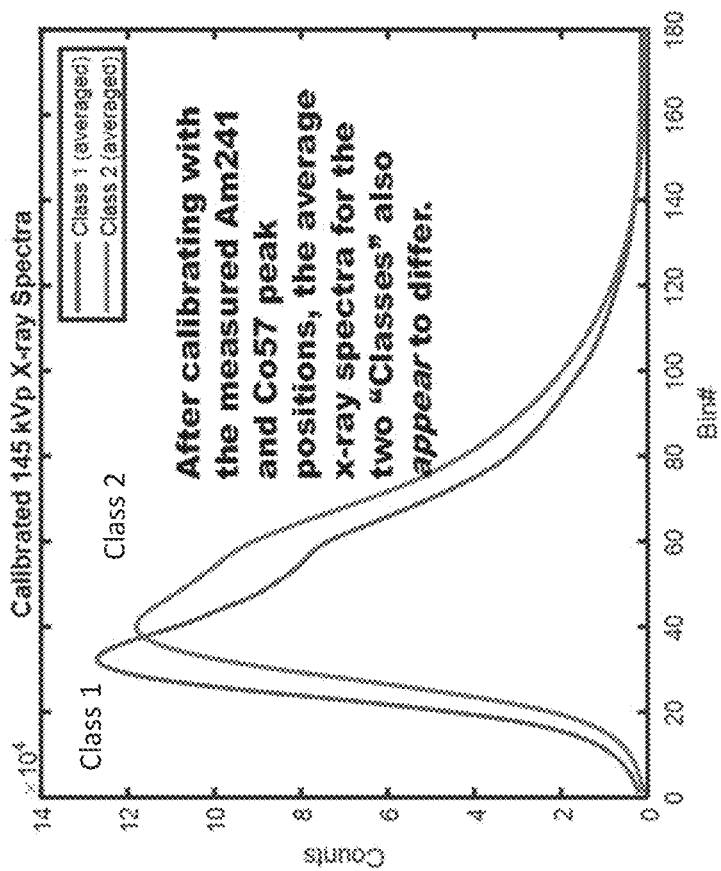
FIGS. 18A and 18B are outputs illustrating two classes of pixels.
Figure 18A:
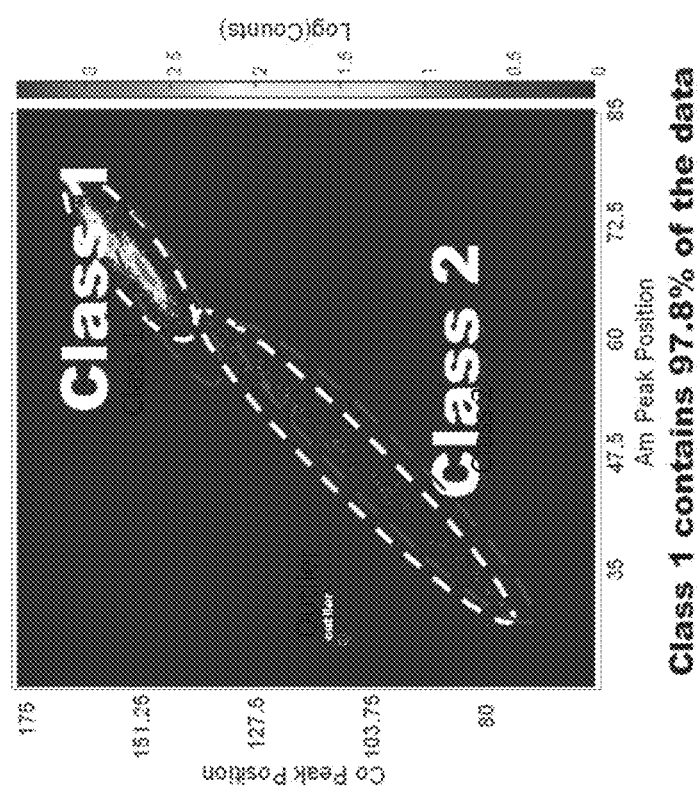

FIGS. 18A and 18B are graphs that illustrate the apparent classes of pixels exhibiting slightly different detector response (see FIG. 12 and corresponding writeup for details). FIG. 18A is a graph of Am241 and Co57 peak positions showing two classes of pixels. FIG. 18B is a graph of calibrated X-ray spectra. As illustrated in FIG. 18B, after being calibrated with the measured Am241 and Co57 peak positions, the average X-ray spectra for the two classes also appear to differ.

In one embodiment, a classifier neural network can be added as a front end to identify the class of each pixel based on the input X-ray spectra data. Two separate neural networks can be trained for each class. The classifier neural network is trained to determine which of the two classes a pixel belongs. In one embodiment, the input X-ray data is first input to the classifier network to determine the class to which each pixel belongs, and then the neural networks that are used to determine the Am241 and Co57 peak positions from the X-ray data are chosen, on a pixel-by-pixel basis, based on the determined pixel class.

Figure 19A:
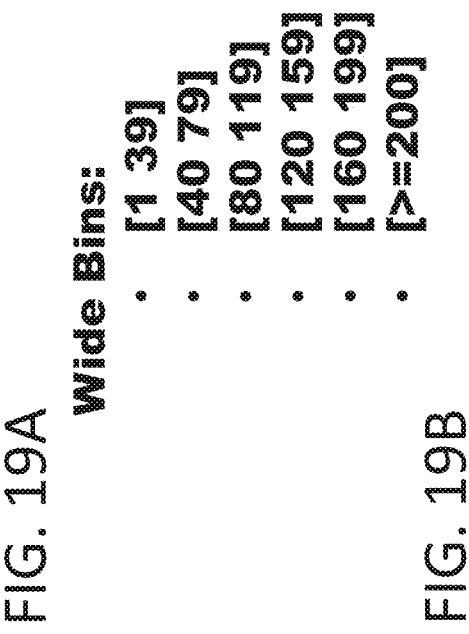
FIGS. 19A and 19B are charts illustrating binning data into wide energy bins for X-ray spectrum with different incident electron energy and ratio of said spectrum.
Figure 19B:
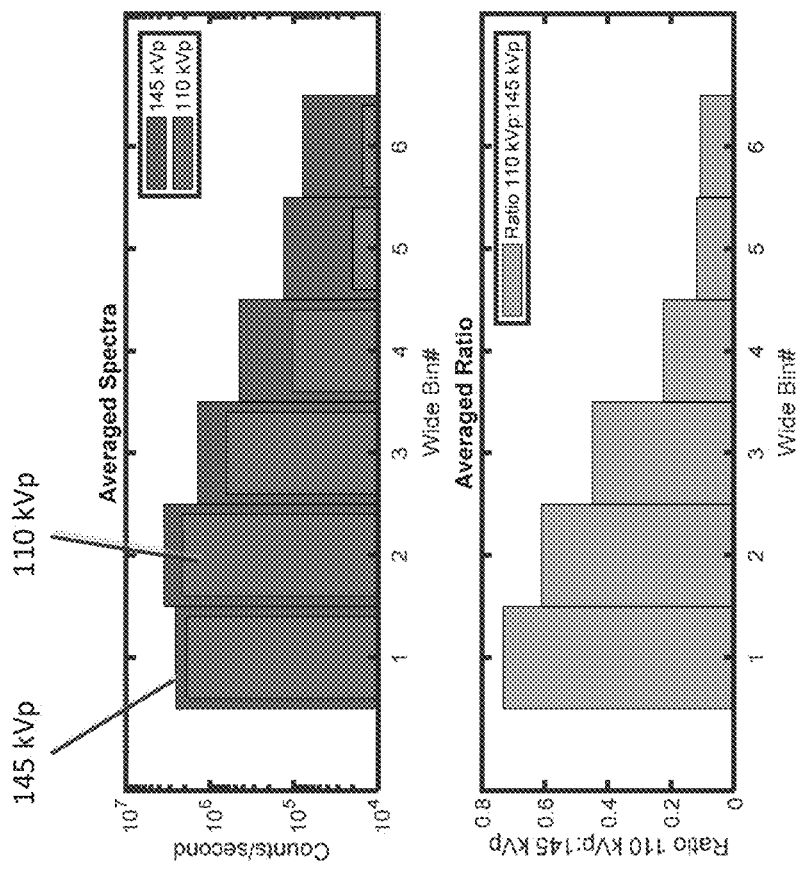

Depending on the particular production version of the CT scanner, different bins sizes (wider or narrower) can be used for the network training to exactly match the CT scanner binning. FIGS. 19A and 19B are charts for energy bins, namely one particular embodiment with six energy bins covering the full energy spectrum of interest. FIG. 19A illustrates binning of the average spectra, while FIG. 19B illustrates binning of the ratio of the two X-Ray spectra 110 keV/145 keV.

In one embodiment, the bins are six wide energy bins, as follows: [1, 39], [40, 79], [80, 119], [120, 159], [160, 199], and [>=200] keV.

Figures 20A, 20B:
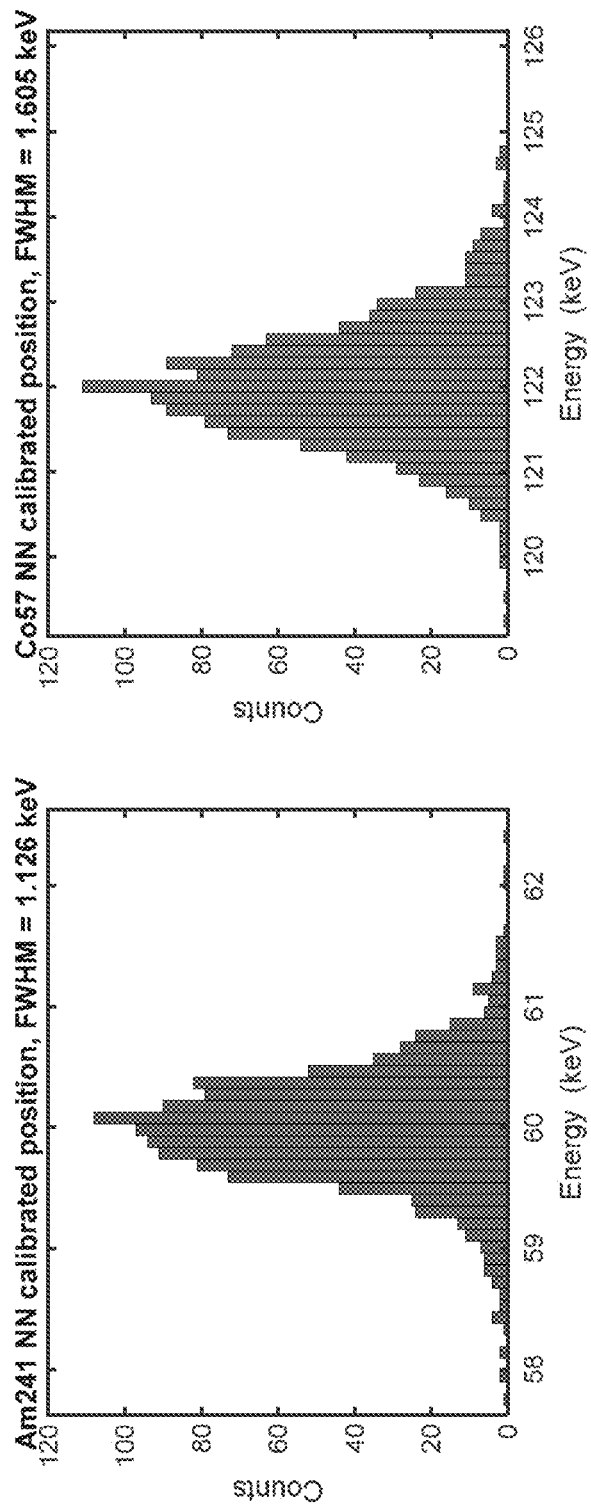
FIGS. 20A and 20B are charts illustrating results of using wide-binned data as input.

FIGS. 20A and 20B are histogram charts of results for input data pre-processed as wide binned data. The histogram charts in FIGS. 20A and 20B show that the Am241 spectrum results are degraded more than the Co57 spectrum results. If different wide bin-widths can be used during calibration, it is likely that a non-uniform width (smaller widths at lower energies) could improve results. In one embodiment, an iterative approach can be used that starts with all bin-boundary settings identical across all pixels in the first iteration, and then changes to different settings for a second iteration (based on the neural network output from the first iteration, with the settings intended to set each pixel's bin boundaries to a similar keV, instead of an arbitrary unit, with two different neural networks used for the two different iterations). Different selections of X-ray kVp (lower value for the low-kVp spectrum) can also help improve the Am241 60 keV results (and the Co57 122 keV results).

Figure 21:
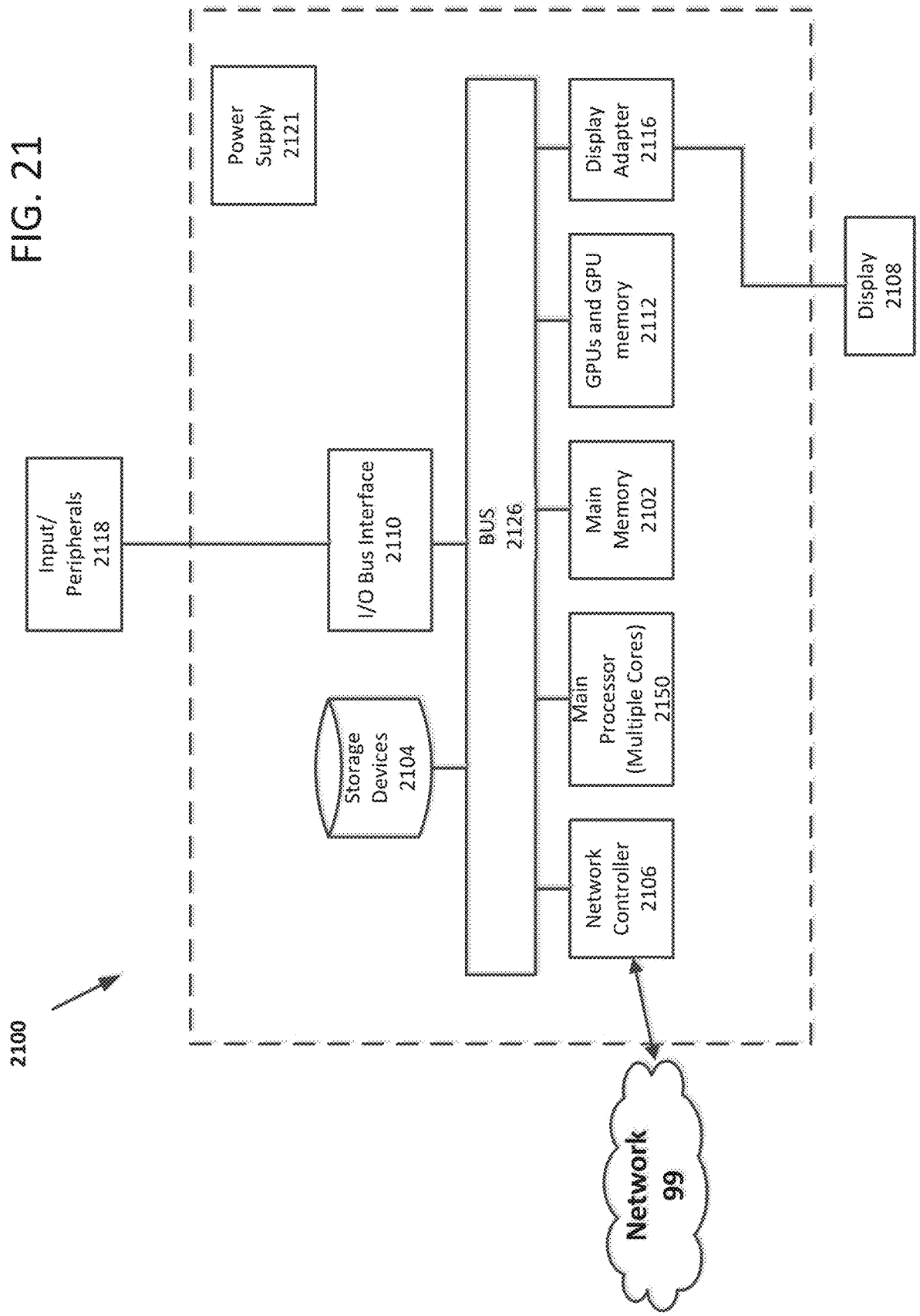
FIG. 21 is a computer system for performing a neural network for calibration of photon counting detector.

FIG. 21 is a block diagram illustrating an example computer system 2100 for implementing the machine learning training and inference methods according to an exemplary aspect of the disclosure. The computer system can be an AI workstation running a server operating system, for example Ubuntu Linux OS, Windows Server, a version of Unix OS, or Mac OS Server. The computer system 2100 includes one or more central processing units (CPU) 2150 having multiple cores. The computer system 2100 can include a graphics board 2112 having multiple GPUs, each GPU having GPU memory. The graphics board 2112 performs many of the mathematical operations of the disclosed machine learning methods. In other embodiments, the computer system 2100 can include a machine learning engine 2112. The machine learning engine 2112 performs many of the mathematical operations of the disclosed machine learning methods. The computer system 2100 includes main memory 2102, typically random access memory RAM, which contains the software being executed by the processing cores 2150 and GPUs 2112, as well as a non-volatile storage device 2104 for storing data and the software programs. Several interfaces for interacting with the computer system 2100 may be provided, including an I/O Bus Interface 2110, Input/Peripherals 2118 such as a keyboard, touch pad, mouse, Display Adapter 2116 and one or more Displays 2108, and a Network Controller 2106 to enable wired or wireless communication through a network 99. The interfaces, memory and processors can communicate over the system bus 2126. The computer system 2100 includes a power supply 2121, which can be a redundant power supply.

In some embodiments, the computer system 2100 includes a CPU and a graphics card, in which the GPUs have multiple cores.

The above-described hardware description is a non-limiting example of corresponding structure for performing the functionality described herein.

Numerous modifications and variations of the present disclosure are possible in light of the above teachings. It is therefore to be understood that within the scope of the appended claims, the invention may be practiced otherwise than as specifically described herein.

The invention claimed is:

1. A method for calibrating a detector, the method comprising:
   acquiring a first energy spectrum obtained from a scan using an X-ray tube as a source of radiation;
   estimating calibration parameters, for each of a plurality of channels of the detector, by applying the acquired first energy spectrum to inputs of a trained neural network that outputs the calibration parameters; and
   calibrating each of the plurality of channels using the estimated calibration parameters.

2. The method of claim 1, wherein the acquiring step further comprises acquiring at least two full-resolution energy spectrum scans at different voltages of the X-ray tube, and
   the estimating step further comprises applying the at least two full-resolution energy spectrum scans to the inputs of the trained neural network.

3. The method of claim 1, wherein in the estimating step, the acquired first energy spectrum applied to the inputs of the trained neural network includes six or fewer energy bins.

4. The method in claim 1, further comprising training the neural network based on particular mechanical or spectral features of the detector.

5. The method of claim 4, further comprising training the neural network based on spatial variation by additionally inputting a position of a channel into the neural network.

6. The method of claim 4, further comprising training the neural network based on bow-tie effects due to a bow-tie filter, wherein the first energy spectrum variation is accounted for by additionally inputting a thickness and a material of the bow-tie filter into the neural network.

7. The method in claim 4, further comprising training the neural network based on a type of bow-tie filter used when acquiring the first energy spectrum.

8. The method in claim 7, wherein the neural network has an input indicating a type of a bow-tie filter used when acquiring the first energy spectrum.

9. The method in claim 7, wherein the neural network has inputs indicating a thickness and a material of a bow-tie filter used when acquiring the first energy spectrum.

10. The method in claim 4, further comprising training the neural network based on a type of spectral filter used when acquiring the first energy spectrum.

11. The method of claim 1, further comprising:
    repeating the acquiring and estimating steps in order to detect changes in the calibration parameters, and
    recalibrating the detector based on the changes in the calibration parameters and established tolerances.

12. The method of claim 1, further comprising:
    augmenting the first energy spectrum to increase an amount of training data; and
    training the neural network using the augmented training data.

13. The method of claim 1, wherein, for each of the plurality of channels, the calibration parameters are a gain and an offset defining a linear function relating measured energy to calibrated energy.

14. The method of claim 1, further comprising:
    training the neural network to output the calibration parameters using training data determined using two or more measurements selected from isotope peak positions, K-edge absorption features, and K-edge emission peaks.

15. A method for calibrating a detector, the method comprising:
    acquiring a first energy spectrum obtained from a scan using an X-ray tube as a source of radiation;

training a plurality of different neural networks for corresponding different spatial regions of the detector;

estimating calibration parameters, for each of a plurality of channels of the detector, by applying the acquired first energy spectrum to corresponding inputs of the plurality of trained neural networks, which output the calibration parameters for the corresponding different spatial regions; and calibrating each of the plurality of channels using the estimated calibration parameters.

16. An apparatus for calibrating a detector, the apparatus comprising:

processing circuitry configured to acquire a first energy spectrum obtained from a scan using an X-ray tube as a source of radiation;

estimate calibration parameters, for each of a plurality of channels of the detector, by applying the acquired first energy spectrum to inputs of a trained neural network device that outputs the calibration parameters; and calibrate each of the plurality of channels using the estimated calibration parameters.

17. The apparatus of claim 16, wherein the processing circuitry is further configured to acquire at least two full-resolution energy spectrum scans at different voltages of the X-ray tube.

18. The apparatus of claim 16, wherein the processing circuitry is further configured to acquire the first energy spectrum for six or fewer energy bins.

19. The apparatus of claim 16, wherein the processing circuitry is further configured to train the neural network based on particular mechanical or spectral features of the detector.

20. The apparatus of claim 19, wherein the processing circuitry is further configured to train the neural network based on spatial variation by additionally inputting a position of a channel into the neural network.

21. The apparatus of claim 19, wherein the processing circuitry is further configured to train the neural network based on bow-tie effects due to a bow-tie filter, wherein the first energy spectrum variation is accounted for by additionally inputting a thickness and a material of the bow-tie filter into the neural network.

22. The apparatus of claim 16, wherein the processing circuitry is further configured to recalibrate the detector based on changes in calibration parameters.

23. The apparatus of claim 16, wherein the processing circuitry is further configured to augment the first energy spectrum to increase an amount of training data; and train the neural network using the augmented training data.

24. The apparatus of claim 16, wherein the processing circuitry is further configured to estimate, for each of the plurality of channels, a gain and an offset as the calibration parameters defining a linear function relating measured energy to calibrated energy.

* * * * *